United States Patent
Puskas et al.

(10) Patent No.: US 6,593,747 B2
(45) Date of Patent: *Jul. 15, 2003

(54) METHOD AND APPARATUS FOR MONITORING ADSORBENT ACTIVITY IN SITU

(75) Inventors: Judit E. Puskas, London (CA); Shahzad Barghi, London (CA)

(73) Assignees: The University of Western Ontario, London (CA); Bayer, Inc., Toronto (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/166,511

(22) Filed: Oct. 5, 1998

(65) Prior Publication Data

US 2002/0021117 A1 Feb. 21, 2002

(51) Int. Cl.⁷ ......................... G01N 27/02; G01N 27/26; G01N 27/00
(52) U.S. Cl. ......................... 324/439; 324/446; 324/663; 324/664; 324/689; 324/693; 324/71.1; 73/61.41
(58) Field of Search ............................... 324/439, 446, 324/663, 664, 689, 693, 694, 71.1; 73/61.41

(56) References Cited

U.S. PATENT DOCUMENTS

3,579,097 A * 5/1971 Luden .................. 324/439
5,282,381 A * 2/1994 Krone-Schmidt ....... 324/693 X
6,090,267 A * 7/2000 Hansen et al. ......... 324/71.1 X

FOREIGN PATENT DOCUMENTS

JP    1-253645    10/1989
SU    1221571 A    3/1986

OTHER PUBLICATIONS

Mousa, M.A. et al.; "Electrical Conduction in γ–Irradiated and Unirradiated $Fc_2O_3$," Materials Chemistry and Physics 11 (1984), 433–441, (Month Unavailable).

* cited by examiner

*Primary Examiner*—N. Le
*Assistant Examiner*—Wasseem H. Hamdan
(74) *Attorney, Agent, or Firm*—Summa & Allan, P.A.

(57) ABSTRACT

The present invention is directed to a method and apparatus of determining the degree of saturation of a decontamination-removing substance or adsorbent such as an alumina absorbent or activated charcoal. The method and apparatus is sufficiently sensitive to detect changes in the bulk specific electrical conductivity of the adsorbent.

27 Claims, 7 Drawing Sheets

Comparison of the Conductivities of Fresh and Used Active Carbon
Voltage drop Measurement. - Packed Bed - VP

Figure 2B

Voltage drop Measurement. - Single bead - VS

Figure 3

Comparison of the Conductivities of Fresh and Used (saturated with $CO_2$) Activated Carbon, Method RS.

METHOD AND APPARATUS FOR MONITORING ADSORBENT ACTIVITY IN SITU

FIELD OF THE INVENTION

The present invention is directed to a method of determining the degree of saturation of an adsorbent material. More particularly, it is directed to measuring changes in conductivity to establish a change in adsorptive capacity.

BACKGROUND OF THE INVENTION

In many industrial processes the moisture content of gaseous streams should be reduced to a very low level, to prevent corrosion (production of dodecylbenzylsulfonic acid used in detergent industry) and/or side reactions (hydrolysis of reactants). Fixed bed dryers are generally used where the moisture content of the gases is reduced by adsorption/absorption on solid sorbents. Water molecules are entrapped in the capillaries on the particle surface. Depending on the type of the adsorbent, unwanted side products might form. In order to avoid the formation of such byproducts, some sorbents must be pretreated. After the pretreatment the sorbent is used on-stream until completely saturated. The saturated sorbent is usually regenerated by desorbing water to be used again for drying. The saturation-drying cycle is repeated many times. A regeneration factor can be defined which shows what percentage of the absorbed water can be removed and what capacity will be available for the next cycle.

%regeneration factor=The amount of desorbed moisture/Total amount of absorbed water (completely saturated)×100

100% regeneration factor means complete removal of the absorbed water.

Other adsorbents such as activated charcoal are used to adsorb hydrocarbon fumes. The activity of the adsorbent gradually decreases as it becomes saturated by hydrocarbons. The spent adsorbent must then be replaced or regenerated. The present invention is directed to a method for determining the relative capacity/activity of activated charcoal based on conductivity measurements.

Conductivity measurements in the solid phase are relatively easy and are used to characterize materials containing ionic species. For instance, the electrical conductivity of pure and doped $Fe_2O_3$, and the effect of gamma-irradiation on the electrical conductivity was studied (M. A. Mousa, E. A. Gomaa, A. A. El-Khouly and A. A. M. Aly: Mater. Chem. Phys. 11, 433 (1984)). Doping either increased or decreased the electrical conductivity of pure $Fe_2O_3$ ($\sigma^*=1.5\times10^{-6}$ [$\Omega^{-1}$ cm$^{-1}$]), depending on the type and amount of doping elements. Gamma-irradiation increased the conductivity of pure $Fe_2O_3$, which in turn decreased upon annealing. Higher doses caused higher conductivity increases, which was explained by increasing charge carrier ($Fe^{2+}$) concentrations. The above mentioned paper investigated these oxides in terms of semiconducting properties.

Soviet Union Patent No. 1221571 discusses monitoring of the decomposition of peroxides using a semiconductor sensor. Free electrons forming during the decomposition of the peroxides affect the electrical properties of the sensor. This differs fundamentally from the present invention in which ionic compounds are involved.

Japanese Patent No. HEI 1-253645 discloses a tube type of bed in which electrodes are placed at the entrance and exit of the tube. In this circuit, the bed represents a certain resistance which is greater than the resistance of the carbon due to voids between particles. When a solvent saturates the bed and fills the cavities, the resistance of the bed decreases. This is essentially the same as shorting out a circuit by moisture; the vapor/liquid provides an alternative conducting route. It is clearly apparent that this method is only useful for measuring gross changes in conductivity.

The present disclosure is directed to a method of measuring changes in conductivity as an indicator of relative adsorbent activity of a sorptive substance, such as an alumina sorbent or a decontaminating substance such as activated charcoal. Resistance is measured on a single bead or in a packed bed. As the degree of adsorption increases, the route of electrons is blocked and the resistance increases. The method of the current invention is capable of detecting changes in conductivity orders of magnitude smaller than the changes detectable by the Japanese method. The high level of sensitivity of the present invention ensures that the degree of saturation can be monitored to ensure that absolutely no break-through occurs. This is essential in industrial applications where the degree of saturation is rarely allowed to exceed 20%. Conductivity measurements are determined in the adsorptive phase. The adsorptive phase is defined as the stage at which all the sorbent is held to the sorptive material by physical or chemical means. Thus, for the present invention, in contrast to the above mentioned Japanese patent, as soon as molecules are in free phase, the adsorptive material is already saturated.

SUMMARY OF THE INVENTION

The present invention is directed to a method of monitoring the relative capacity of adsorbents at various stages of saturation by measuring an electrical property of the adsorbent and correlating a value for conductivity to adsorptive capacity. Changes in conductivity are determined during the adsorptive phase in which the material to be adsorbed is bound to the adsorptive material by physical or chemical means.

BRIEF DESCRIPTION OF THE DRAWINGS

The invention is described in more detail herein with reference to the accompanying drawings, in which.

DESCRIPTION OF THE PREFERRED EMBODIMENTS

The present invention is concerned with easy monitoring methods to follow and interpret the electrical properties, such as specific conductivity or resistance, of various adsorbent materials. The data disclosed herein and detailed in the examples below demonstrate that conductivity measurements are a reliable indicator of the degree of exhaustion of the adsorbent materials, such as alumina adsorbents and activated charcoal. The novel method is sensitive enough to detect minute changes in the bulk specific electrical conductivity of the adsorbents.

Figure 6:
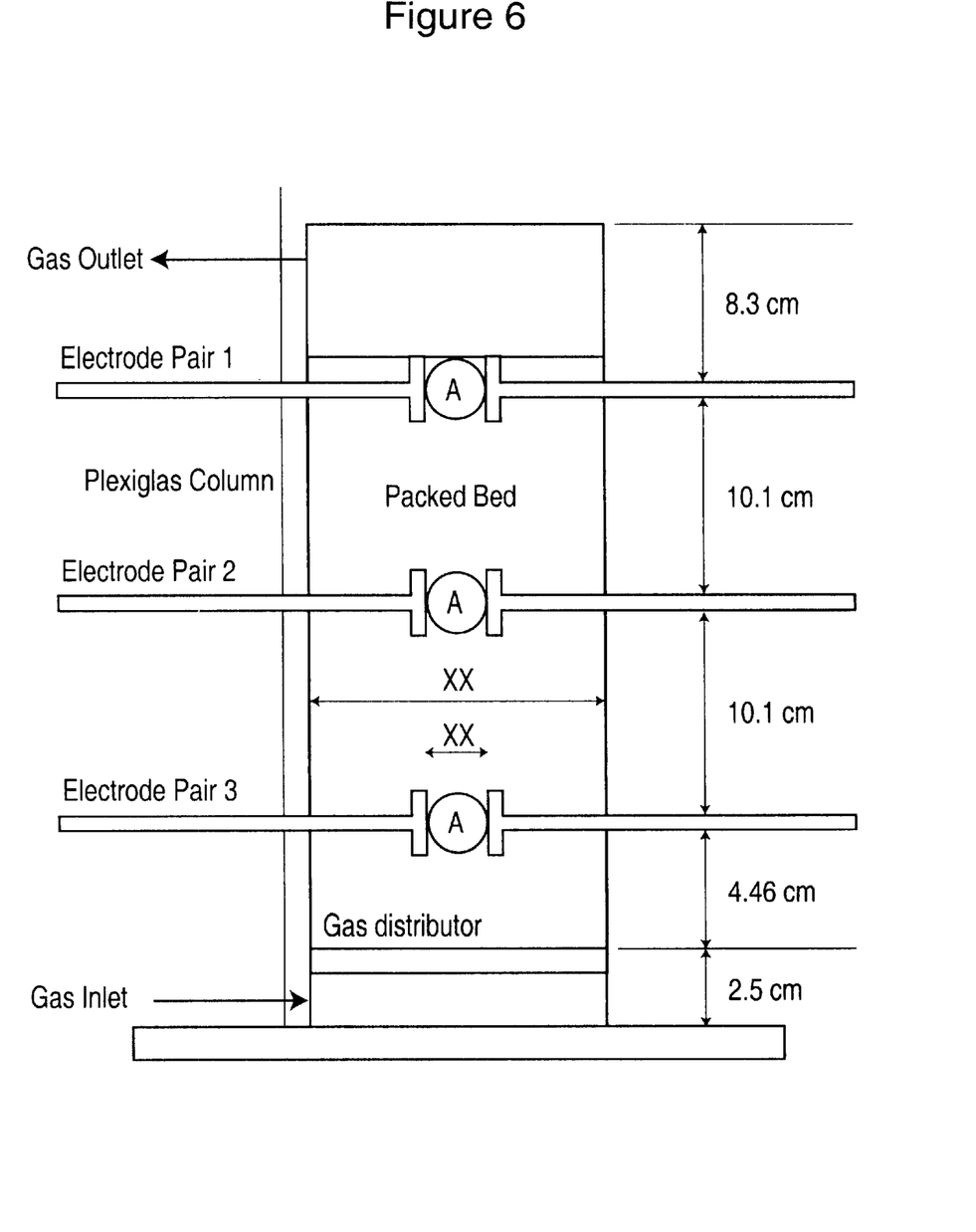
FIGS. 6 and 7 are schematics of apparatus that may be used in the practice of the invention.
Figure 7:
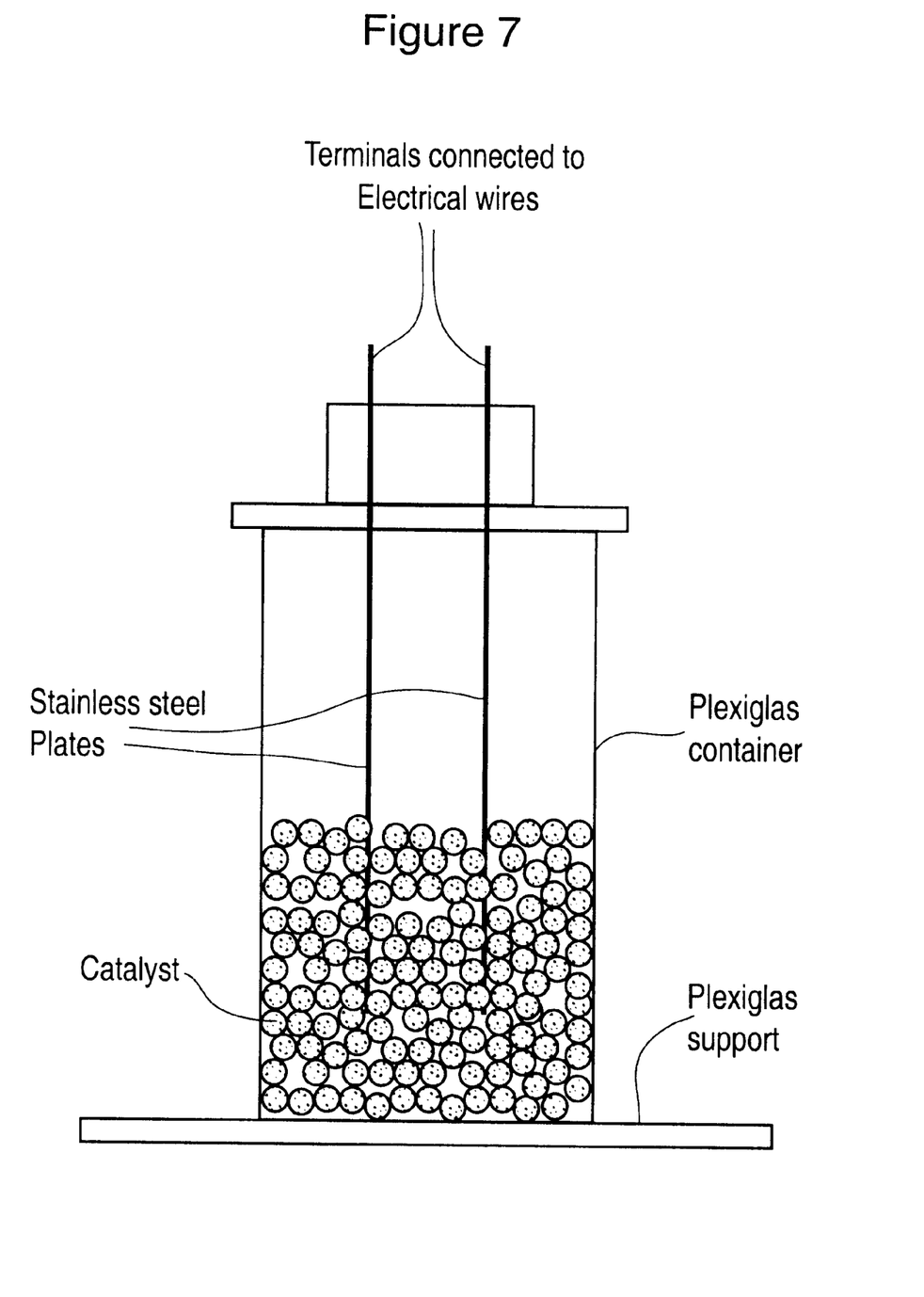

One method for determining an electrical property of the adsorbent which relates to conductivity, measures the d.c. resistance of a single bead while another method measures the d.c. resistance of a packed bed between two parallel plates. The resistance was either measured directly or by measuring the voltage drop across the catalyst (single bead or packed bed). FIGS. 6 and 7 are schematics of apparatus that may be used in the practice of the invention.

The following abbreviations will be used to describe the various methods:

RS=direct resistance measurement, single bead
RP=direct resistance measurement, packed bed
VS=voltage drop measurement, single bead
VP=voltage drop measurement, packed bed The resistance is obtained from calibration curves constructed by using known resistors as $R_x$, to account for the internal impedance of the electrometer (Keithley Model 600 B).

The direct resistance measurement and the voltage drop measurement yield identical values within experimental error as expected. The resistance in a packed bed is a combination of the resistance of the beads and the voids (in this case air). The specific conductivity $\sigma^*$ ($Scm^{-1}$ or $\Omega^{-1}cm^{-1}$) is calculated from equation 1:

$$R=1/\sigma^*L/A \qquad (1)$$

where L and A are the length and the cross section of the resistor in cm and $cm^2$, respectively. In case of a single bead average bead dimensions are used; in case of the packed bed L is the distance of the parallel plates (L=1.2 cm) and A is the surface of the electrodes immersed in the bed (A=4 $cm^2$).

Conductivity measurements do not differentiate between conductive species, but from the practical point of view it is enough to pinpoint a change signaling saturation. As sorbent binds to an adsorptive material, the conductivity may increase or decrease. The direction of the change depends upon the innate resitivity of the starting material and the relative conductivities of the adsorptive material and the sorb ant. We have found the surprising result that conductivity does change during the adsorptive phase and that changes can be detected when the level of saturation of the adsorptive material is low, typically less than 20% saturated. This surprising result is further demonstrated in the following examples.

Alumina adsorbents were tested by the method of the present invention. The results discussed in Examples 1 through 14 demonstrate that the conductivity changes correlate with the capacity of alumina adsorbents. Activated charcoal used for adsorbing hydrocarbon fumes was also tested by the present invention and the results are discussed in Example 15. Experiments were also conducted to evaluate the use of the method to determine adsorption of carbon dioxide and to determine its applicability to molecular sieve technology.

EXAMPLES

The above disclosure generally describes the invention. A more complete understanding can be obtained by reference to the following specific examples. These examples are described solely for purposes of illustration and are not intended to limit the scope of the invention.

Example 1

A commercial pretreated alumina adsorbent (AL12) was investigated. The conductivity of the pretreated adsorbent was RS-8.17×10$^{-9}$ and VS=8.09×10$^{-9}$ [$\Omega^{-1}$ cm$^{-1}$] on a single bead. The conductivity of the saturated adsorbent was measured to be two orders of magnitude higher than that of the pretreated adsorbent—RS=6.85×10$^{-7}$; VS=6.45×10$^{-7}$ [$\Omega^{-1}$ cm$^{-1}$]. This sample was regenerated, and the conductivity of the regenerated sample was 7.62×10$^{-9}$ [$\Omega^{-1}$ cm$^{-1}$]. The results are summarized in Table I below.

TABLE I

| Test # | Pretreated, $(\Omega\text{-cm})^{-1} \times 10^9$ | Saturated, $(\Omega\text{-cm})^{-1} \times 10^7$ |
|---|---|---|
| 1 | 3.47 | 1.67 |
| 2 | 9.62 | 3.13 |
| 3 | 7.58 | 0.96 |
| 4 | 20.83 | 2.08 |
| 5 | 9.62 | 2.78 |
| 6 | 5.56 | 11.90 |
| 7 | 4.90 | 8.62 |
| 8 | 6.94 | 13.89 |
| 9 | 3.42 | 8.06 |
| 10 | 52.08 | 1.39 |
| STDEV | 14.82 | 4.77 |
| Average | 8.09 | 6.45 |

Figure 1:
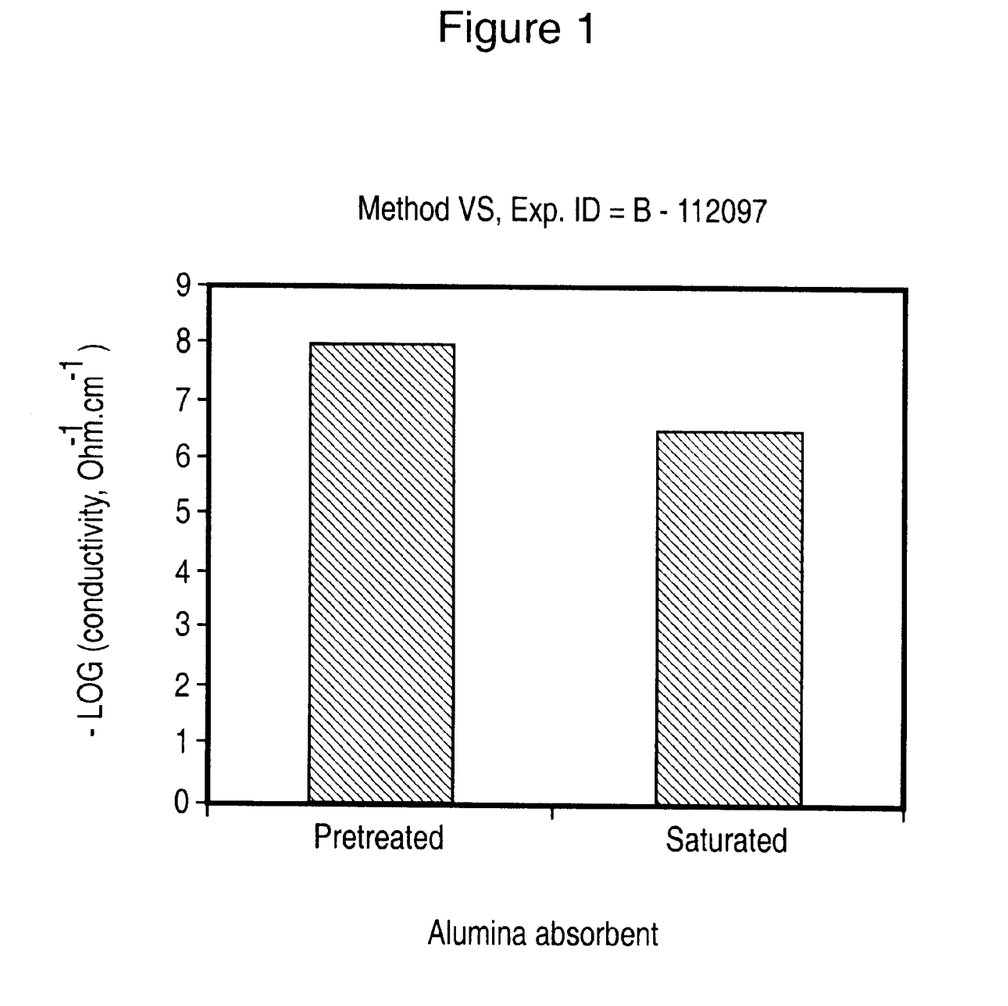
FIG. 1 illustrates a comparison of the conductivities of pretreated and saturated alumina adsorbent.

FIG. 1 illustrates graphically a comparison between the pretreated and saturated samples. The regeneration cycle was repeated three times for this sample and nearly complete regeneration was observed as shown below in Table II.

The large difference between the conductivities of unsaturated and saturated adsorbent demonstrate the feasibility of the method of the present invention for indicating exhaustion.

Example 2

A commercial pretreated alumina adsorbent, AL13 was investigated. The conductivity of the pretreated adsorbent was RS=5.57×10$^{-9}$ [$\Omega^{-1}$ cm$^{-1}$] on a single bead. The conductivity of the saturated adsorbent was measured to be two orders of magnitude higher than that of the pretreated adsorbent—RS=3.76×10$^{-7}$ [$\Omega^{-1}$ cm$^{-1}$]. This sample was regenerated, and the cycle was repeated three times for this sample and nearly complete regeneration was observed as shown in Table II for sample AL13.

TABLE II

Regeneration data of alumina gel samples

| Sample Code/No. Description | First Regen. | Regeneration factor Second Regen. | Third Regen. | Conductivity $(\Omega\text{-cm})^{-1}$ |
|---|---|---|---|---|
| AL12 | 98.7 | 98.4 | 98.6 | 7.62E-9 |
| AL13 | 99.5 | 98.6 | 98.3 | 5.54E-9 |
| AL14 | 99.3 | 99.5 | 98.4 | 8.18E-9 |
| AL15 | 98.2 | 98.8 | 97.9 | 1.42E-12 |

Example 3

A commercial pretreated alumina adsorbent, AL14 was investigated. The conductivity of the pretreated adsorbent was RS=9.46×10$^{-9}$ [$\Omega^{-1}$ cm$^{-1}$] on a single bead. The conductivity of the saturated adsorbent was measured to be two orders of magnitude higher than that of the pretreated adsorbent—RS=8.61×10$^{-7}$ [$\Omega^{-1}$ cm$^{-1}$]. This sample was regenerated, and the conductivity of the regenerated sample was $8.18 \times 10^{-9}$ $[\Omega^{-1}\ cm^{-1}]$. The regeneration cycle was repeated three times for this sample and nearly complete regeneration was observed as shown above in Table II.

Example 4

A commercial alumina adsorbent (AL15) was investigated. The conductivity of the unused adsorbent was RS=$3.75 \times 10^{-12}$ $[\Omega^{-1}\ cm^{-1}]$ on a single bead. The conductivity of the saturated adsorbent was measured to be two orders of magnitude higher than that of the unused adsorbent—RS=$1.47 \times 10^{-10}$ $[\Omega^{-1}\ cm^{-1}]$. This sample was regenerated, and the conductivity of the regenerated sample was $1.42 \times 10^{-12}$ $[\Omega^{-1}\ cm^{-1}]$ as shown in Table II.

Example 5

A commercial alumina (AL2) adsorbent was investigated. The conductivity of the unused adsorbent was RS=$7.60 \times 10^{-12}$ $[\Omega^{-1}\ cm^{-1}]$ on a single bead. The conductivity of the saturated adsorbent was measured to be two orders of magnitude higher than that of the unused adsorbent—RS=$5.63 \times 10^{-10}$ $[\Omega^{-1}\ cm^{-1}]$. This sample was regenerated, and the conductivity of the regenerated sample was $1.86 \times 10^{-12}$ $[\Omega^{-1}\ cm^{-1}]$. The regeneration cycle was repeated three times for this sample and nearly complete regeneration was observed.

Example 6

A commercial alumina (AL3) adsorbent was investigated. The conductivity of the unused adsorbent was RS=$5.26 \times 10^{-11}$ $[\Omega^{-1}\ cm^{-1}]$ on a single bead. The conductivity of the saturated adsorbent was measured to be two orders of magnitude higher than that of the unused adsorbent—RS=$7.83 \times 10^{-9}$ $[\Omega^{-1}\ cm^{-1}]$. This sample was regenerated, and the conductivity of the regenerated sample was $5.65 \times 10^{-11}$ $[\Omega^{-1}\ cm^{-1}]$.

Example 7

A commercial alumina (AL4) adsorbent was investigated. The conductivity of the unused adsorbent was RS=$7.91 \times 10^{-11}$ $[\Omega^{-1}\ cm^{-1}]$ on a single bead. The conductivity of the saturated adsorbent was measured to be two orders of magnitude higher than that of the unused adsorbent—RS=$8.65 \times 10^{-9}$ $[\Omega^{-1}\ cm^{-1}]$. This sample was regenerated, and the conductivity of the regenerated sample was $3.67 \times 10^{-11}$ $[\Omega^{-1}\ cm^{-1}]$.

Example 8

A commercial alumina (AL5) adsorbent was investigated. The conductivity of the unused adsorbent was RS=$8.70 \times 10^{-11}$ $[\Omega^{-1}\ cm^{-1}]$ on a single bead. The conductivity of the saturated adsorbent was measured to be two orders of magnitude higher than that of the unused absorbent—RS=$2.28 \times 10^{-10}$ $[\Omega^{-1}\ cm^{-1}]$. This sample was regenerated, and the conductivity of the regenerated sample was $3.85 \times 10^{-11}$ $[\Omega^{-1}\ cm^{-1}]$.

Example 9

A commercial alumina (AL6) adsorbent was investigated. The conductivity of the unused adsorbent was RS=$6.06 \times 10^{-11}$ $[\Omega^{-1}\ cm^{-1}]$ on a single bead. The conductivity of the saturated adsorbent was measured to be two orders of magnitude higher than that of the unused adsorbent—RS=$8.58 \times 10^{-9}$ $[\Omega^{-1}\ cm^{-1}]$. This sample was regenerated, and the conductivity of the regenerated sample was $4.48 \times 10^{-11}$ $[\Omega^{-1}\ cm^{-1}]$.

Example 10

A commercial alumina (AL7) absorbent was investigated. The conductivity of the unused adsorbent was RS=$4.24 \times 10^{-11}$ $[\Omega^{-1}\ cm^{-1}]$ on a single bead. The conductivity of the saturated adsorbent was measured to be two orders of magnitude higher than that of the unused adsorbent—RS=$8.61 \times 10^{-9}$ $[\Omega^{-1}\ cm^{-1}]$. This sample was regenerated, and the conductivity of the regenerated sample was $4.13 \times 10^{-11}$ $[\Omega^{-1}\ cm^{-1}]$.

Example 11

A commercial alumina (AL8) adsorbent was investigated. The conductivity of the unused adsorbent was RS=$1.65 \times 10^{-9}$ $[\Omega^{-1}\ cm^{-1}]$ on a single bead. The conductivity of the saturated adsorbent was measured to be two orders of magnitude higher than that of the unused adsorbent—RS=$6.44 \times 10^{-7}$ $[\Omega^{-1}\ cm^{-1}]$. This sample was regenerated, and the conductivity of the regenerated sample was $1.72 \times 10^{-9}$ $[\Omega^{-1}\ cm^{-1}]$.

Example 12

A commercial pretreated alumina (AL9) adsorbent was investigated. The conductivity of the pretreated adsorbent was RS=$3.04 \times 10^{-9}$ $[\Omega^{-1}\ cm^{-1}]$ on a single bead. The conductivity of the saturated adsorbent was measured to be close to that of the pretreated adsorbent—RS=$1.05 \times 10^{-9}$ $[\Omega^{-1}\ cm^{-1}]$. This sample was regenerated, and the conductivity of the regenerated sample was $2.68 \times 10^{-9}$ $[\Omega^{-1}\ cm^{-1}]$. This sample appeared to be totally exhausted.

Example 13

A commercial pretreated alumina (AL10) adsorbent was investigated. The conductivity of the pretreated adsorbent was RS=$1.56 \times 10^{-10}$ $[\Omega^{-1}\ cm^{-1}]$ on a single bead. The conductivity of the saturated adsorbent was measured to be two orders of magnitude higher than that of the pretreated adsorbent—RS=$3.48 \times 10^{-8}$ $[\Omega^{-1}\ cm^{-1}]$. This sample was regenerated, and the conductivity of the regenerated sample was $2.24 \times 10^{-11}$ $[\Omega^{-1}\ cm^{-1}]$ Example 14

A commercial pretreated alumina (AL 11) adsorbent was investigated. The conductivity of the pretreated absorbent was RS=$9.52 \times 10^{-11}$ $[\Omega^{-1}\ cm^{-1}]$ on a single bead. The conductivity of the saturated adsorbent was measured to be two orders of magnitude higher than that of the pretreated adsorbent—RS=$7.12 \times 10^{-9}$ $[\Omega^{-1}\ cm^{-1}]$. This sample was regenerated, and the conductivity of the regenerated sample was $9.13 \times 10^{-11}$ $[\Omega^{-1}\ cm^{-1}]$. The results of all 14 samples are summarized in Tables II and III.

TABLE III

Results of alumina absorbent samples

| Sample Code/No. | Electrical Conductivity | | Regeneration factor | Conductivity after Regen. $(\Omega\text{-cm})^{-1}$ |
|---|---|---|---|---|
| | Unsaturated $(\Omega\text{-cm})^{-1}$ | Saturated $(\Omega\text{-cm})^{-1}$ | | |
| AL2 | 7.60E-12 | 5.63E-10 | 98.2 | 1.86E-12 |
| AL3 | 5.26E-11 | 7.83E-9 | 92.7 | 5.65E-11 |
| AL4 | 7.91E-11 | 8.65E-9 | 98.5 | 3.67E-11 |
| AL5 | 8.70E-11 | 2.28E-10 | 93.4 | 3.85E-11 |
| AL6 | 6.06E-11 | 8.58E-9 | 97.9 | 4.48E-11 |
| AL7 | 4.42E-11 | 8.61E-9 | 88.5 | 4.13E-11 |

TABLE III-continued

Results of alumina absorbent samples

| Sample Code/No. | Electrical Conductivity | | Regeneration factor | Conductivity after Regen. ($\Omega$-cm)$^{-1}$ |
|---|---|---|---|---|
| | Unsaturated ($\Omega$-cm)$^{-1}$ | Saturated ($\Omega$-cm)$^{-1}$ | | |
| AL8  | 1.65E-9   | 6.44E-7  | 92.6 | 1.72E-9  |
| AL9  | 3.04E-9   | 1.05E-9  | —    | 2.68E-9  |
| AL10 | 1.56E-10  | 3.49E-8  | 96.6 | 2.24E-9  |
| AL11 | 9.52E-11  | 7.12E-9  | 98.2 | 9.13E-11 |
| AL12 | 8.17E-9   | 6.85E-7  | 98.7 | 7.62E-9  |
| AL13 | 5.57E-9   | 3.76E-7  | 99.5 | 5.54E-9  |
| AL14 | 9.46E-9   | 8.61E-7  | 99.3 | 8.18E-9  |
| AL15 | 3.75E-12  | 1.47E-10 | 95.6 | 1.42E-12 |

Example 15

Figure 2A:
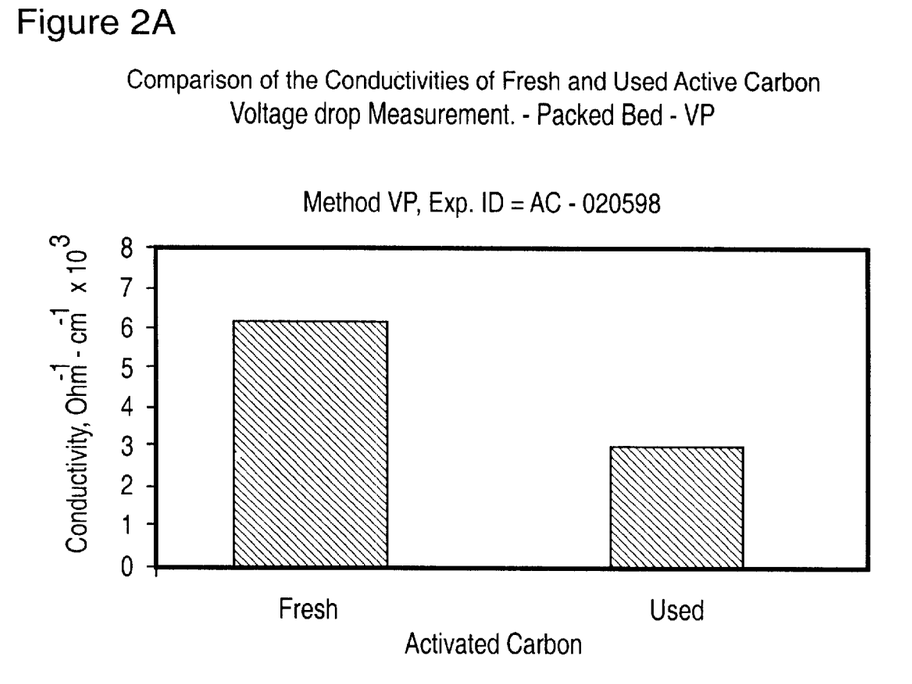
FIGS. 2A and 2B illustrate a comparison of the conductivities of fresh and used active carbon for a packed bed and a single bead.
Figure 2B:
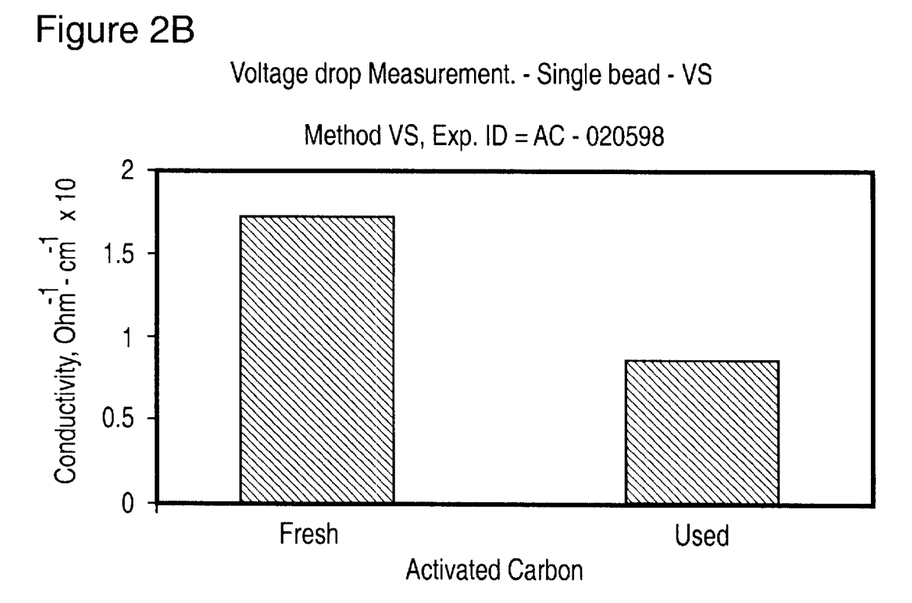

Activated charcoal (Fluka, EC 2311533) used for the adsorption of hydrocarbon fumes was investigated. The conductivity of the fresh charcoal was RS=1.78×10$^{-1}$ and VS=1.72×10$^{-1}$ [$\Omega^{-1}$ cm$^{-1}$] on a single cylindrical bead(L=0.61 cm; A=0.14 cm$^2$), and RP=6.61×10$^{-3}$ and VP=6.21×1$^{-3}$ [$\Omega^{-1}$ cm$^{-1}$] in a packed bed. The conductivity of the hydrocarbon-saturated charcoal was measured to be less than half of that of the fresh one—RS=8.16×10$^{-2}$; VS=8.55×10$^{-2}$, RP=3.02×10$^{-3}$ and VP=3.04×10$^{-3}$ [$\Omega^{-1}$ cm$^{-1}$]. The data are summarized in Tables IVa and IVb, and the comparison is shown graphically in FIG. 2. Thus this method can be a sensitive measure of the exhaustion of activated charcoal adsorbent beds used frequently in the chemical industry.

TABLE IVA

Conductivity Data of Active Carbon Single Bead

| Test # | Fresh [$\Omega$-cm]$^{-1}$ × 10$^{-1}$ | Used [$\Omega$-cm]$^{-1}$ × 10$^{-2}$ |
|---|---|---|
| 1       | 2.22 | 9.50  |
| 2       | 1.47 | 9.65  |
| 3       | 1.85 | 7.45  |
| 4       | 2.39 | 9.14  |
| 5       | 2.13 | 7.69  |
| 6       | 1.22 | 8.00  |
| 7       | 1.62 | 7.61  |
| 8       | 1.45 | 7.32  |
| 9       | 1.27 | 10.18 |
| 10      | 1.60 | 8.92  |
| STDEV   | 0.41 | 1.05  |
| Average | 1.72 | 8.55  |

TABLE IVb

Packed Bed

| Test # | Fresh [$\Omega$-cm]$^{-1}$ × 10$^{-3}$ | Used [$\Omega$-cm]$^{-1}$ × 10$^{-3}$ |
|---|---|---|
| 1       | 6.74 | 3.10 |
| 2       | 6.61 | 2.90 |
| 3       | 6.38 | 2.98 |
| 4       | 5.31 | 3.12 |
| 5       | 5.70 | 3.21 |
| 6       | 6.90 | 3.07 |
| 7       | 6.20 | 2.89 |
| 8       | 6.48 | 2.87 |
| 9       | 6.37 | 3.05 |
| 10      | 5.43 | 3.16 |
| STDEV   | 0.55 | 0.12 |

TABLE IVb-continued

Packed Bed

| Test # | Fresh [$\Omega$-cm]$^{-1}$ × 10$^{-3}$ | Used [$\Omega$-cm]$^{-1}$ × 10$^{-3}$ |
|---|---|---|
| Average | 6.21 | 3.04 |

Example 16

Figure 3:
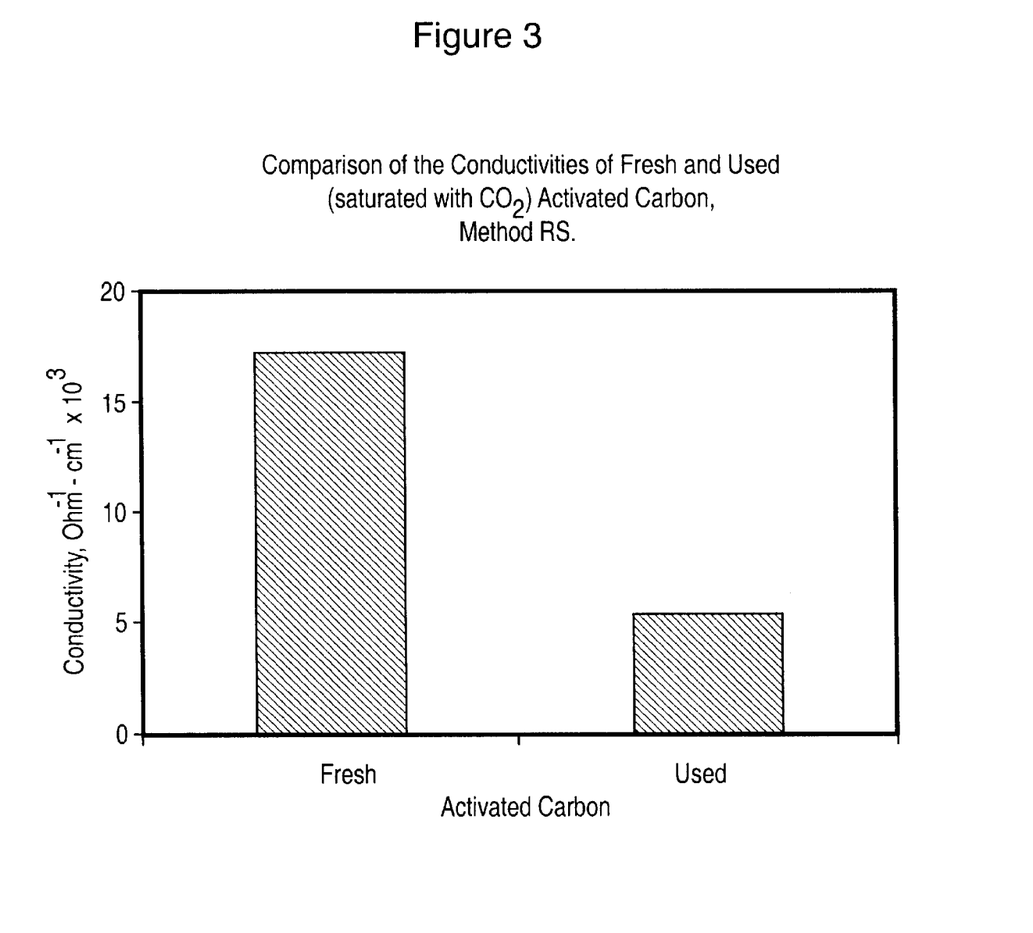
FIG. 3 illustrates the effect on conductivity when $CO_2$ is adsorbed to activated carbon.

The adsorption of carbon dioxide on activated charcoal was investigated. The conductivity of the fresh activated carbon was RS=1.72×10$^{-2}$ [$\Omega^{-1}$ cm$^{-1}$]. The conductivity of the used adsorbent was 5.18×10$^{-3}$ [$\Omega^{-1}$ cm$^{-1}$]. The results are shown below in Table V and are illustrated graphically in FIG. 3.

TABLE V

Conductivity Data for the adsorption of CO$_2$ on Activated Carbon Method RS

| Test # | Fresh [$\Omega$-cm]$^{-1}$ × 10$^{-2}$ | Used [$\Omega$-cm]$^{-1}$ × 10$^{-3}$ |
|---|---|---|
| 1       | 1.69 | 5.04 |
| 2       | 1.80 | 5.19 |
| 3       | 1.74 | 5.28 |
| 4       | 1.69 | 5.25 |
| 5       | 1.65 | 5.21 |
| 6       | 1.78 | 5.20 |
| 7       | 1.71 | 5.13 |
| 8       | 1.76 | 5.07 |
| 9       | 1.69 | 5.22 |
| 10      | 1.72 | 5.23 |
| STDEV   | 0.05 | 0.08 |
| Average | 1.72 | 5.18 |

Example 17

Figure 4:
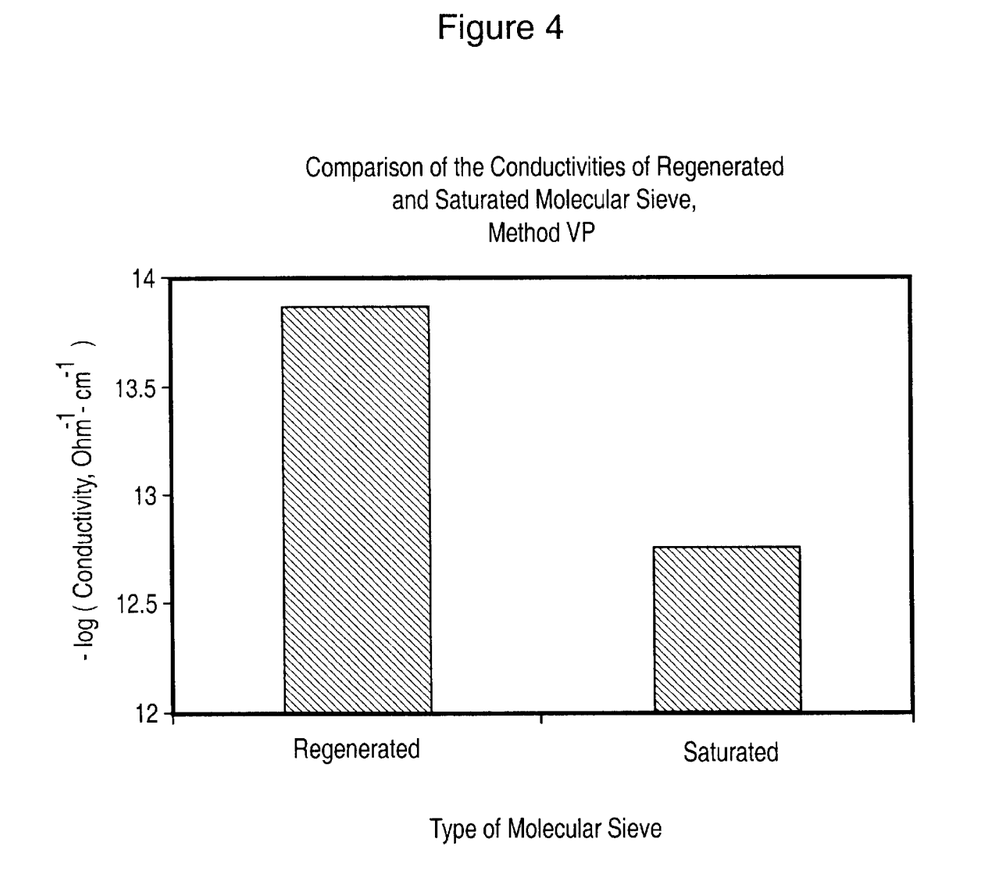
FIG. 4 illustrates a comparison of the conductivities of regenerated and saturated molecular sieve in a packed bed configuration.
Figure 5:
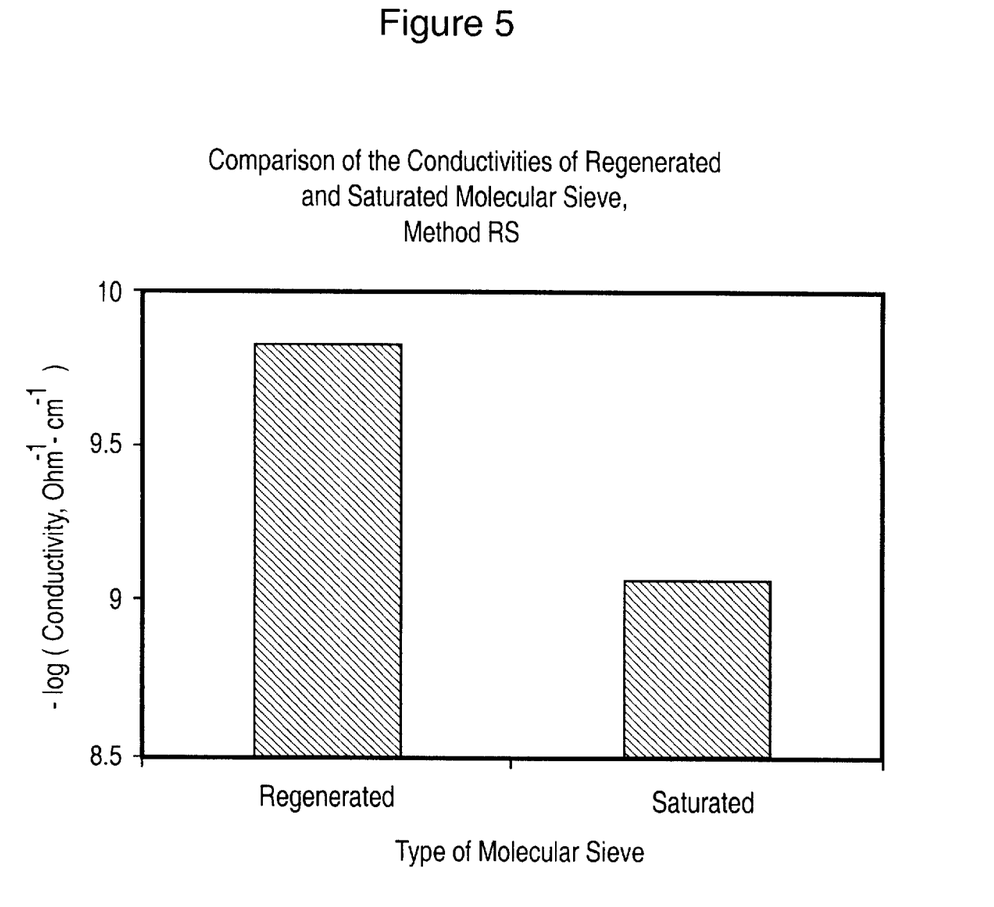
FIG. 5 illustrates a comparison of regenerated and saturated molecular sieve on a single bead.

The adsorption of water on a molecular sieve was investigated. In a packed bed, the conductivity of the fresh sieve was 1.25×10$^{-14}$ [$\Omega^{-1}$ cm$^{-1}$] and the conductivity of the used adsorbent was 1.72×10$^{-13}$ [$\Omega^{-1}$ cm$^{-1}$]. The conductivity of the fresh adsorbent was 2.14×10$^{-9}$ [$\Omega^{-1}$ cm$^{-1}$] on a single bead while the used adsorbent had a conductivity of 2.01×10$^{-10}$ [$\Omega^{-1}$ cm$^{-1}$]. The results are shown in Tables VIa and VIb below and are illustrated graphically in FIGS. 4 and 5.

TABLE VIa

Molecular Sieve Conductivity Data Method VP (Packed Bed)

| Test # | Fresh [$\Omega$-cm]$^{-1}$ × 10$^{-14}$ | Used [$\Omega$-cm]$^{-1}$ × 10$^{-13}$ |
|---|---|---|
| 1       | 1.32  | 1.67  |
| 2       | 1.19  | 2.86  |
| 3       | 1.43  | 1.47  |
| 4       | 1.47  | 1.92  |
| 5       | 1.18  | 1.72  |
| 6       | 1.16  | 1.61  |
| 7       | 1.28  | 1.54  |
| 8       | 1.23  | 1.69  |
| 9       | 1.14  | 1.67  |
| 10      | 1.19  | 1.63  |
| STDEV   | 0.115 | 0.914 |
| Average | 1.25  | 1.72  |

TABLE VIb

Molecular Sieve Conductivity Data
Method RS (Single Bead)

| Test # | Fresh [Ω-cm]$^{-1}$ × 10$^{-9}$ | Used [Ω-cm]$^{-1}$ × 10$^{-10}$ |
|---|---|---|
| 1 | 6.25 | 2.38 |
| 2 | 5.00 | 3.57 |
| 3 | 3.33 | 1.52 |
| 4 | 1.00 | 1.06 |
| 5 | 1.54 | 0.50 |
| 6 | 2.00 | 1.00 |
| 7 | 0.63 | 1052 |
| 8 | 0.59 | 5.56 |
| 9 | 0.71 | 1.54 |
| 10 | 0.35 | 2.04 |
| STDEV | 2.06 | 1.49 |
| Average | 2.14 | 2.07 |

Although preferred embodiments of the invention have been described herein in detail, it will be understood by those skilled in the art that variations may be made thereto without departing from the spirit of the invention or the scope of the appended claims.

What is claimed is:

1. A method for evaluating the capacity of an adsorptive material to adsorb a substance, said method comprising monitoring electrical conductivity in situ of said adsorptive material between at least one pair of spaced essentially parallel electrode plates within a bed of adsorptive material wherein there is a progressive change in conductivity as said substance binds to said adsorptive material and wherein said change can be detected at levels of overall saturation as low as 20% and wherein said step of monitoring conductivity of said adsorptive material comprises measuring an electrical property of said adsorptive material which relates to said electrical conductivity.

2. The method of claim 1 wherein said measured electrical property is resistivity and wherein measured resistivity is correlated with adsorptive capacity.

3. The method of claim 2, wherein said resistivity is d.c. resistance.

4. A method of claim 1, wherein said measured electrical property is capacitance and correlating measured capacitance with adsorptive capacity.

5. A method of claim 1 wherein said electrical conductivity of said adsorptive material is monitored over time to determine a change in electrical conductivity of said material, correlating a change in conductivity with a decrease in adsorptive capacity and correlating an opposite change in conductivity with an increase in adsorptive capacity.

6. A method of claim 5 wherein a determined extent of decrease in conductivity correlates with said adsorptive material being saturated.

7. A method of claim 5 wherein a determined extent of increase in conductivity correlates with said adsorptive material being regenerated.

8. A method of claim 1 wherein said electrical property is measured on a single particle of adsorptive material.

9. A method of claim 1 wherein said electrical property is measured "in situ" of a bed of adsorptive material in a treatment unit.

10. A method of claim 9 wherein said electrical property is measured between two spaced apart electrodes positioned in a bed of said adsorptive material.

11. A method of claim 1 wherein said electrical property is measured "in situ" of a bed of adsorptive material in a regenerator unit.

12. A method of claim 10 wherein said electrical property is measured between two spaced apart electrodes positioned in a bed of said adsorptive material.

13. A method of claim 1 wherein said adsorptive material is selected from the group consisting of activated carbon, alumina adsorbents and molecular sieve.

14. A method of claim 13 wherein said adsorptive material is activated carbon.

15. A method of claim 13 wherein said adsorptive material is aluminum oxide.

16. An apparatus for determining the adsorptive capacity of an adsorptive material, said apparatus comprising:

i) a pair of spaced electrodes for monitoring electrical conductivity of the adsorptive material; and a processor for correlating adsorptive capacity with measured electrical conductivity of an adsorptive material comprising:

i) means for receiving a signal from said pair of spaced electrodes representative of surface electrical conductivity, and ii) programmable means for generating adsorptive capacity information based on a monitored value for conductivity.

17. An apparatus of claim 16 wherein said monitoring means comprises spaced apart electrodes in contact with a particulate adsorptive material.

18. An apparatus of claim 17 wherein said spaced apart electrodes are adapted to be placed in a bed of particulate adsorptive material to measure conductivity thereof.

19. An apparatus of claim 16 further comprising means for retaining an adsorptive particle between said electrodes.

20. An apparatus of claim 19 wherein said retaining means biases said electrodes against an adsorptive particle.

21. An apparatus of claim 16 wherein said correlating means includes means for generating adsorptive capacity information based on a monitored value for conductivity.

22. An apparatus of claim 21 wherein said monitoring means determines at any point in time a value for electrical conductivity and said capacity information generating means providing a corresponding value for adsorptive capacity.

23. An apparatus of claim 21 wherein said monitoring means monitors electrical conductivity over time to determine a change in electrical conductivity of said adsorptive material, said capacity information generating means correlating a change in conductivity with a decrease in adsorptive capacity and correlating an opposite change in conductivity with an increase in adsorptive capacity.

24. An apparatus of claim 23 wherein said capacity information generating means is programmed to correlate a determined extent of increase in conductivity with an adsorptive material being saturated, said adsorptive material being aluminum oxide.

25. An apparatus of claim 23 wherein said capacity information generating means is programmed to correlate a determined extent of increase in conductivity with an adsorptive material being saturated, said adsorptive material being activated carbon.

26. An adsorptive tower having an apparatus of claim 16 for monitoring adsorptive capacity in said tower.

27. An adsorptive material regenerator having an apparatus of claim 16 for monitoring adsorptive material capacity during an adsorptive regeneration cycle.

* * * * *